(12) United States Patent
Mangold et al.

(10) Patent No.: US 9,638,624 B2
(45) Date of Patent: May 2, 2017

(54) METHOD FOR REDUCING INTERFERENCE FRINGES IN LASER SPECTROSCOPY MEASUREMENTS USING AN ABSORPTION MASK IN COMBINATION WITH MULTI-PASS OPTICAL CELLS

(71) Applicant: EMPA EIDGENÖSSISCHE MATERIALPRÜFUNGS- UND FORSCHUNGSANSTALT, Dübendorf (CH)

(72) Inventors: Markus Mangold, Dübendorf (CH); Bela Tuzson, Dübendorf (CH); Lukas Emmenegger, Dübendorf (CH)

(73) Assignee: EMPA EIDGENÖSSISCHE MATERIALPRÜFUNGS- UND FORSCHUNGSANSTALT, Dübendorf (CH)

( * ) Notice: Subject to any disclaimer, the term of this patent is extended or adjusted under 35 U.S.C. 154(b) by 50 days.

(21) Appl. No.: 14/434,171

(22) PCT Filed: Oct. 7, 2013

(86) PCT No.: PCT/EP2013/070805
§ 371 (c)(1),
(2) Date: Apr. 8, 2015

(87) PCT Pub. No.: WO2014/056835
PCT Pub. Date: Apr. 17, 2014

(65) Prior Publication Data
US 2015/0300942 A1   Oct. 22, 2015

(30) Foreign Application Priority Data

Oct. 8, 2012   (CH) ........................ 1884/12

(51) Int. Cl.
*G01N 21/03*   (2006.01)
*G01N 21/3504*   (2014.01)

(52) U.S. Cl.
CPC ....... *G01N 21/031* (2013.01); *G01N 21/3504* (2013.01); *G01N 2201/064* (2013.01)

(58) Field of Classification Search
USPC ........................................................ 356/437
See application file for complete search history.

(56) References Cited

U.S. PATENT DOCUMENTS 5,267,019 A * 11/1993 Whittaker ................. G01J 3/02
                                                  250/343
5,636,035 A *  6/1997 Whittaker ............. G01J 3/4338
                                                  250/343

(Continued)

FOREIGN PATENT DOCUMENTS

GB      2120784      12/1983
SE    EP 2136190    * 12/2009

OTHER PUBLICATIONS

International Search Report dated Dec. 17, 2013 for PCT/EP2013/070805.

(Continued)

*Primary Examiner* — Yara B Green
(74) *Attorney, Agent, or Firm* — Paul D. Bianco; Gary S. Winer; Fleit Gibbons Gutman Bongini & Bianco PL

(57) ABSTRACT

A Multi-pass optical cell (1) with an internal space (11) for laser spectroscopy is described, which is able to reduce or eliminate interference fringes appearing by performing laser absorption spectroscopy in the multi-pass optical cells (1) leading to improved absorption spectra. This is achieved by using a multi-pass optical cell (1) comprising an absorption mask (3) which is permanently or removable mountable in the internal space (11) in a rotatably fixed manner, where in a mask wall (30) a plurality of m apertures (300) is formed, (Continued)

in which the position of each aperture (300) is adapted to a predefinable propagation path of a main optical beam and/or the resulting reflection spot pattern (211) defined by the geometry of the multi-pass optical cell (1) and the used angle of incidence of an initial beam (20), so that each aperture (300) is traversable by the main optical beam from a first side (301) to a second side (302).

13 Claims, 5 Drawing Sheets

(56) References Cited

U.S. PATENT DOCUMENTS

| | | | |
|---|---|---|---|
| 6,181,426 B1 * | 1/2001 | Bender | G01N 21/3504 356/432 |
| 7,876,443 B2 | 1/2011 | Bernacki | |
| 2010/0079760 A1 | 4/2010 | Bernacki | |

OTHER PUBLICATIONS

Witten Opinion of the International Searching Authority dated Apr. 8, 2015 for PCT/EP2013/070805.
John U. White; "Long Optical Paths of Large Aperture;" J.O.S.A.; May 1942; pp. 285-288; vol. 32.
D. Herriott, et al.; "Off-Axis Paths in Spherical Mirror Interferometers;" Applied Optics; Apr. 1964; pp. 523-526; vol. 3; No. 4.
J. Barry McManus, et al.; "Dual quantum cascade laser trace gas instrument with astigmatic Herriott cell at high pass number;" Applied Optics; Feb. 1, 2011; pp. A74-A85; vol. 50; No. 4.

* cited by examiner

FIG. 1a
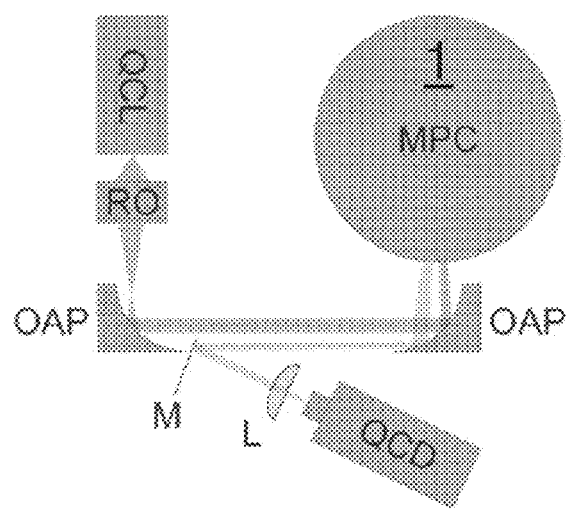
FIG. 1b
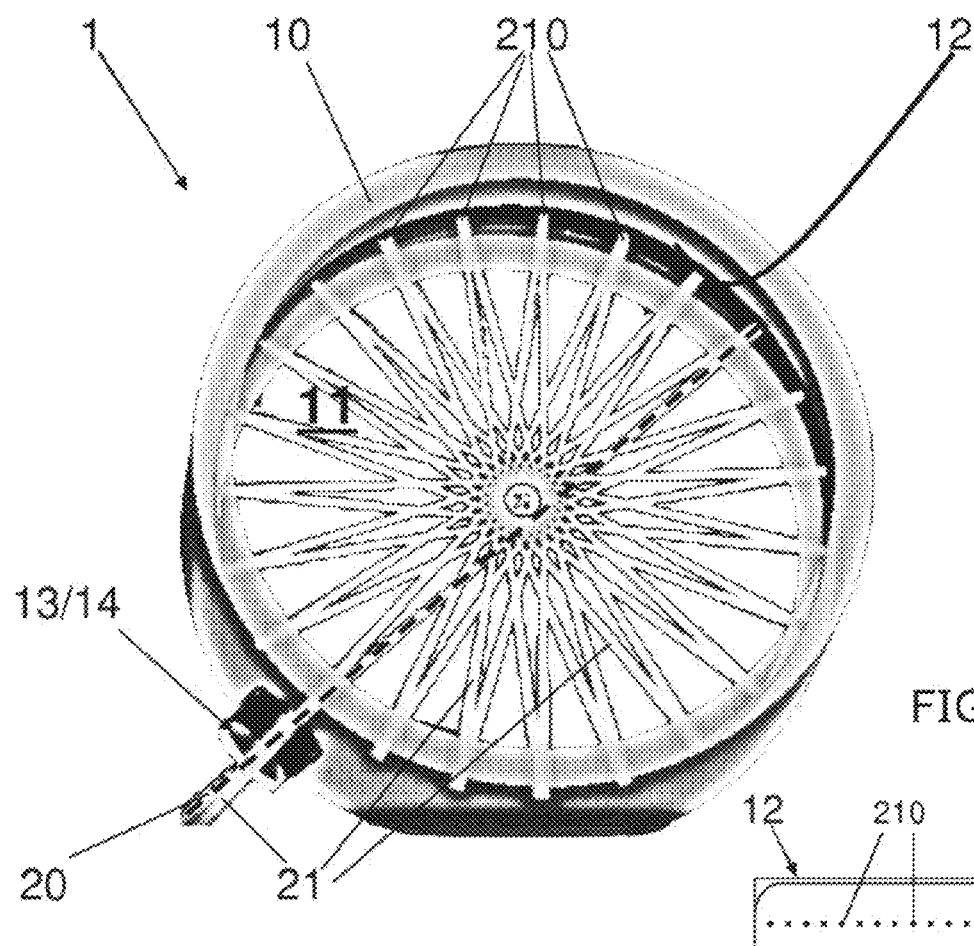
FIG. 1c

METHOD FOR REDUCING INTERFERENCE FRINGES IN LASER SPECTROSCOPY MEASUREMENTS USING AN ABSORPTION MASK IN COMBINATION WITH MULTI-PASS OPTICAL CELLS

TECHNICAL FIELD

The present invention describes a multi-pass optical cell with an internal space for laser spectroscopy, the use of an absorption mask in the internal space of a multi-pass optical cell for laser spectroscopy, as well as a method for reducing interference fringes in laser spectroscopy measurements using a multi-pass optical cell.

STATE OF THE ART

Trace gas measurements based on optical absorption techniques of infrared light are used for a long time. Mid-infrared (MIR) laser spectroscopy (approximately 4000-400 $cm^{-1}$/2.5-25 μm) is widely used to monitor trace gas species in industrial, medical, and environmental applications.

There are several optical resonators known with different designs, known as multi-pass optical cells or multi-pass absorption cells. To achieve high instrumental sensitivity and analytical precision, small absorption signals are usually compensated for by the use of multi-pass optical cells. These multi-pass optical cells are compact, with small dimensions capable to achieve very long optical path lengths.

From an entrance hole an initial beam is reflected between at least one reflective surface. After a certain number of reflections, resulting in a certain number of reflection spots respectively in a reflection spot pattern on the reflective surface, the reflected beam leaves the multi-pass optical cell through an exit hole. The initial beam and the reflected beam are building a main optical beam restricted to a predefined space along a controlled extended path through the mutli-pass optical cell, defined by the cell geometry and the incidence angle of the initial beam. After passing the exit hole, the beam is aimed to an optical detector, where specific changes in the properties of the beam due to interaction with for example a gas sample are detected.

State of the art multi-pass cells are based on the designs of White [J. U. White, J. Opt. Soc. Am. 32, 285 (1942)] and Herriott [D. Herriott, H. Kogelnik, R. Kompfner, Appl. Opt. 3, 523 (1964)], or they use combinations of cylindrical or astigmatic mirrors. All types of multi-pass optical cells contain at least one reflective surface reflecting a light beam multiple times in the cell providing an optical path that is longer than the physical dimension of the multi-pass optical cell. This increases absorption and, therefore, decreases detection limits to more easily detect trace gases in low concentration.

As can be read in U.S. Pat. No. 7,876,443 a multi-pass optical cell consisting of at least one seamless, toroidal ring mirror was proposed. This ring mirror contains one or several openings which serve as entrance and/or exit apertures for a light beam. The light beam is reflected multiple times from the seamless optical surface. Thereby, a long optical path inside a small detection volume is obtained. Depending on the number of reflections the length of the optical path can be changed From the shown computer simulations different reflection spot pattern are achieved.

In all the known multi-pass optical cells as well the toroidal ring mirror optical cell, the stray light can easily propagate through the multi-pass optical cell on a different path than the main optical beam due to the seamless optical surface. At the beam entrance and beam exit aperture, the stray light is combined with the main optical beam and it reaches the detector. Due to the coherent nature of the used laser light, the combination of the different optical paths leads to interference phenomena. The interference appears as strong fringes in the absorption spectrum. These fringes may hide the real absorption features.

To eliminate fringes produced by interference of the main optical beam crossing the internal space of a multi-pass optical cell, methods are known, which are based on the physical translation of reflective surfaces relative to one another. Due to a variation of the length of the main optical beam path, interference fringes can be reduced or eliminated. These setups are complex using additional vibration-inducing devices, for example piezoelectric transducer, which have to be controlled with a vibration control system. For eliminating fringes by physical translation of reflective surface, the multi-pass optical cell has to consist of a plurality of reflective surfaces, which are moveable relatively to another. Therefore interference fringes in multi-pass optical cells with monolithic mirrors similar to the embodiments known from the U.S. Pat. No. 7,876,443 cannot be eliminated.

DESCRIPTION OF THE INVENTION

The object of the present invention is to reduce or eliminate interference fringes appearing by performing laser absorption spectroscopy in multi-pass optical cells, improving the absorption spectra of the prior art.

Another object of the invention is to reach the reduction or elimination of interference fringes appearing by performing laser absorption spectroscopy, independent of the used form of multi-pass optical cell. The solution presented can be adapted to work in any kind of multi-pass optical cell and is therefore a universal solution.

The here disclosed solution is an absorption mask, comprising the features of the independent claim 1, a multi-pass optical cell for laser spectroscopy comprising such an absorption mask, the use of an absorption mask in the internal space of a multi-pass optical cell for laser spectroscopy and the method for reducing interference fringes in laser spectroscopy measurements.

The absorption mask and therewith equipped multi-pass optical cells are applicable in medical applications, for example human breath analysis with MIR laser absorption spectroscopy as a compact spectrometer. A ring mirror absorption cell in combination with an absorption mask facilitates the construction of a compact device for medical applications.

Also environmental applications are of interest and possible. Trace gas monitoring is important to track the development of ambient air composition. For a ubiquitous measurement network, mobile (compact as well as light-weight) spectrometers are needed, which can be constructed with ring mirror absorption cells in combination with the absorption mask.

BRIEF DESCRIPTION OF THE DRAWINGS

The invention will now be described in more detail with reference to specific embodiments thereof and to the accompanying drawings, wherein:

FIG. 1a shows a used Mid-infrared laser absorption spectrometer setup, while

FIG. 1b shows perspective view of a used multi-pass optical cell and

FIG. 1c shows a schematic plane projection of the reflective surface with reflection spots and pattern.

FIG. 2a shows a perspective view of one multi-pass optical cell in the ring mirror design with inserted absorption mask, while

FIG. 4a shows a perspective view of another embodiment of an absorption mask in a one-piece closed ring form, while FIG. 4b shows a perspective view of an absorption mask in a one-piece open ring form with equal sized notches, while

DESCRIPTION

Figure 2A:
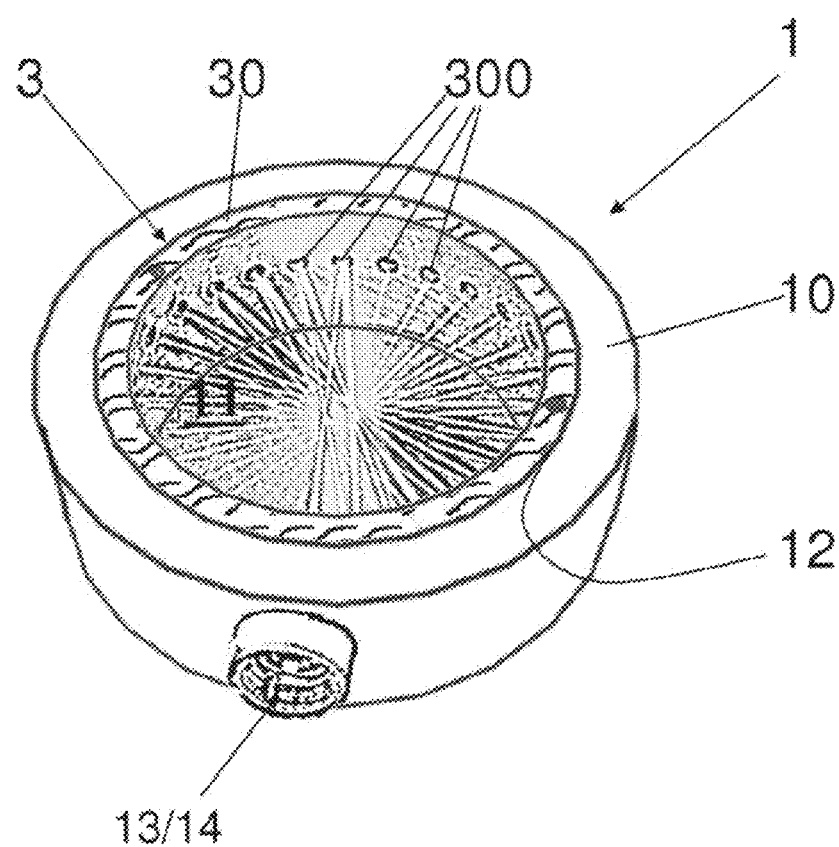
Figure 2B:
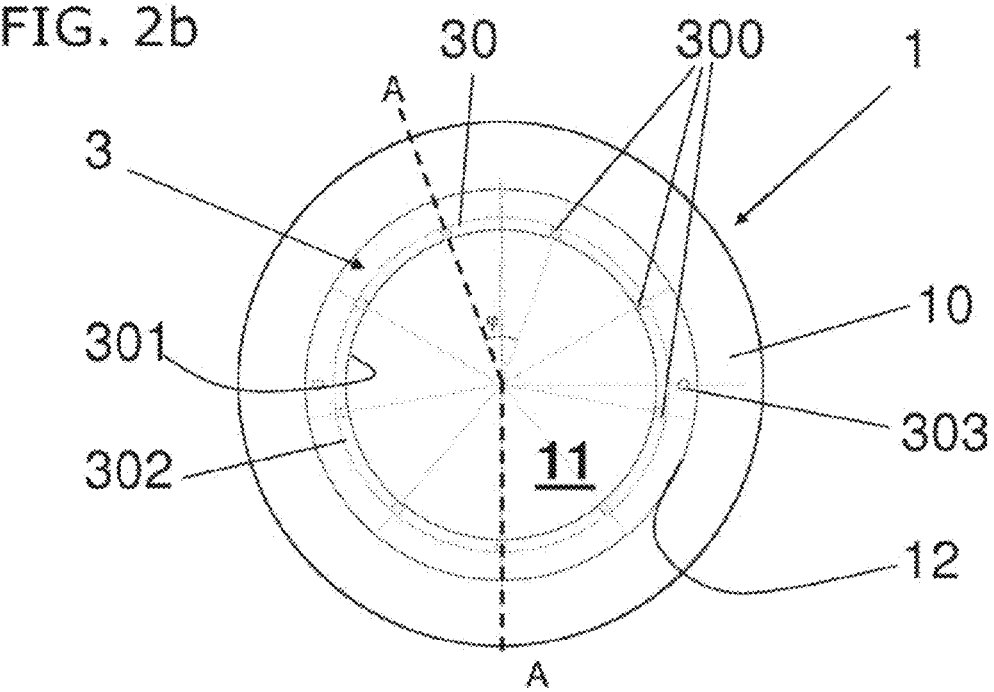
FIG. 2b shows a top view of the multi-pass cell according to FIG. 2a and FIG. 2c shows an aligned sectional view of the multi-pass optical cell along the cutting-plane line A-A of FIG. 2b.

Mid-infrared (MIR) laser spectroscopy, with wavelength between 2.5 to 25 µm is widely used to monitor trace gas species in industrial, medical, and environmental applications. Also known as the spectral fingerprint region, MIR laser spectroscopy is especially attractive because it contains the strong fundamental ro-vibrational bands. Especially in combination with room temperature, continuous wave quantum cascade lasers, MIR laser spectroscopy allows for excellent selectivity, sensitivity, and precision.

An experimental setup used for MIR laser spectroscopy is depicted in FIG. 1a. For the MIR laser spectroscopy measurements a laser beam is generated by a quantum cascade laser QCL. A reflective objective RO and two off-axis parabolic mirrors OAP are used to shape the laser beam. A multi-pass optical cell 1, MPC contains the sample gas. The collimated output beam is guided by a mirror M and focalized by a lens L onto a quantum cascade detector QCD. The preferred wavelength range is 3 to 10 µm.

A preferred multi-pass optical cell 1 here used, comprising a cell body 10 in form of a copper cylinder is exemplary described. A reflective surface 12 is carved into the inner cylinder face, facing the internal space 11 of the multi-pass optical cell, providing a toroidal mirror as one reflective surface 12. The copper cylinder is gold plated to reach higher reflectivity and a chemically inert reflective surface 12, which is resistant against gases.

The cell body 10 and the reflective surface 12 are formed from one piece, therefore the reflective surface 12 is performed in a seamless way. Such a multi-pass optical cell 1 is very robust and it can be produced at low costs.

This cell body 10 contains a beam entrance 13 and a beam exit 14 opening which serve as entrance and/or exit apertures for a light beam. In FIG. 1b simulation of the complete light path from the beam entrance 13 passing the internal space 12 and the exit through the beam exit 14 is shown. An initial beam 20 is coupled through the beam entrance 13 into the internal space 11. In this setup the reflected beams 21 are reflected only in one radial plane in which the carved reflective surface 12 is formed. At each reflection from the reflective surface 12, resulting in a reflection spot 210, the reflected beam 21 is refocalized. This leads to minimal aberration of the laser beam after multiple reflections. The reflected beam 21 is reflected multiple times from the seamless reflective surface 12. Thereby, a long optical path inside a small detection volume is obtained.

Due to the planar light distribution in the internal space 12 of the multi-pass optical cell 1 a planar reflection spot pattern 211 results. Thanks to the planar light distribution in the cell, a small detection volume combined with a robust and easy optical alignment is obtained. In the current configuration, with a 80 mm diameter multi-pass optical cell 1 we achieve an optical path of more than 4 m in a sample volume of less than 40 ml. The excellent path to volume ratio leads to a fast response to changes in the gas composition.

In order to reduce or eliminate interference fringes arising from stray light, an infrared light absorption mask 3 is placed in the internal space 11 of the multi-pass optical cell 1. The absorption mask 3 can either be permanently attached or removable mounted to the internal space 11 of the multi-pass optical cell 1, while the absorption mask 3 has to be attached or mounted in a rotatably fixed manner.

In this example the absorption mask 3 is removable mounted to the internal space 11, more precisely in contact with the cylindrical reflective surface 12.

The absorption mask 3 is carried out self-supporting and dimensionally stable, comprising a mask wall 30. This mask wall 30 has to be mounted in a rotatably fixed manner in a position relative to the predefined propagation path of the main optical beam.

A multitude of apertures 300, completely traversing the mask wall 30 from a first side 301 to a second side 302 of the absorption mask 3, is recessed. The apertures 300 are laminary distributed and adapted to the expected reflection spot pattern 211 of the used multi-pass optical cell 1. When using a multi-pass optical cell 1 according to FIG. 1b, the apertures 300 are distributed in a radial plane over the mask wall 30, having fixed cross sectional areas.

The apertures are provided in such a way that the main optical beam, comprising the initial beam 20 and the reflected beams 21, is unhindered reflected forming a reflection spot pattern 211 on the reflective surface 12 and can pass the absorption mask 3 and the multi-pass optical cell 1 completely unhindered from the beam entrance 13 to the beam exit 14.

After passing the beam entrance 13 the initial beam 20 is entering the internal space 11 in an incident angle relative to the normal. The initial beam 20 is passing the internal space 11 and another aperture 300 on the opposite side of the multi-pass cell 1. After passing the mask wall 30 the initial beam 20 is reflected in a reflection spot 210 on the reflective surface 12 leading to a reflected beam 21. The reflected beam 21 is passing the same aperture 300 due to known laws of geometrical optics under an angle given by the angle of incidence. After a predetermined number n of reflections the reflected beam 21 will pass an aperture 300 a last time and will propagate through the beam exit 14 out of the multi-pass optical cell 1.

The positions of the apertures 300 have to be adapted to the geometry of the multi-pass cell 1 and the angle of incidence of the initial beam 20, which define the propagation path of the main optical beam through the internal space 11 and the expected reflection spot pattern 211 on the reflective surface 12.

In this embodiment of the absorption mask 3 the incoming beam of each reflection spot 210 and the reflected beam of the same reflection spot 210 are passing the same aperture 300. This due to the small distance of the mask wall 30 of the absorption mask 3 from the reflective surface 12. Each aperture 300 lays in the region of each reflection spot 210.

For easy insertion and removal of the absorption mask 3 from the internal space 11, handling means can be attached to the absorption mask 3. These handling means can be molded to the mask wall 30 used as a grip. It is also possible to engage a screw in at least one bore hole 303 to handle the absorption mask 3.

Figure 2C:
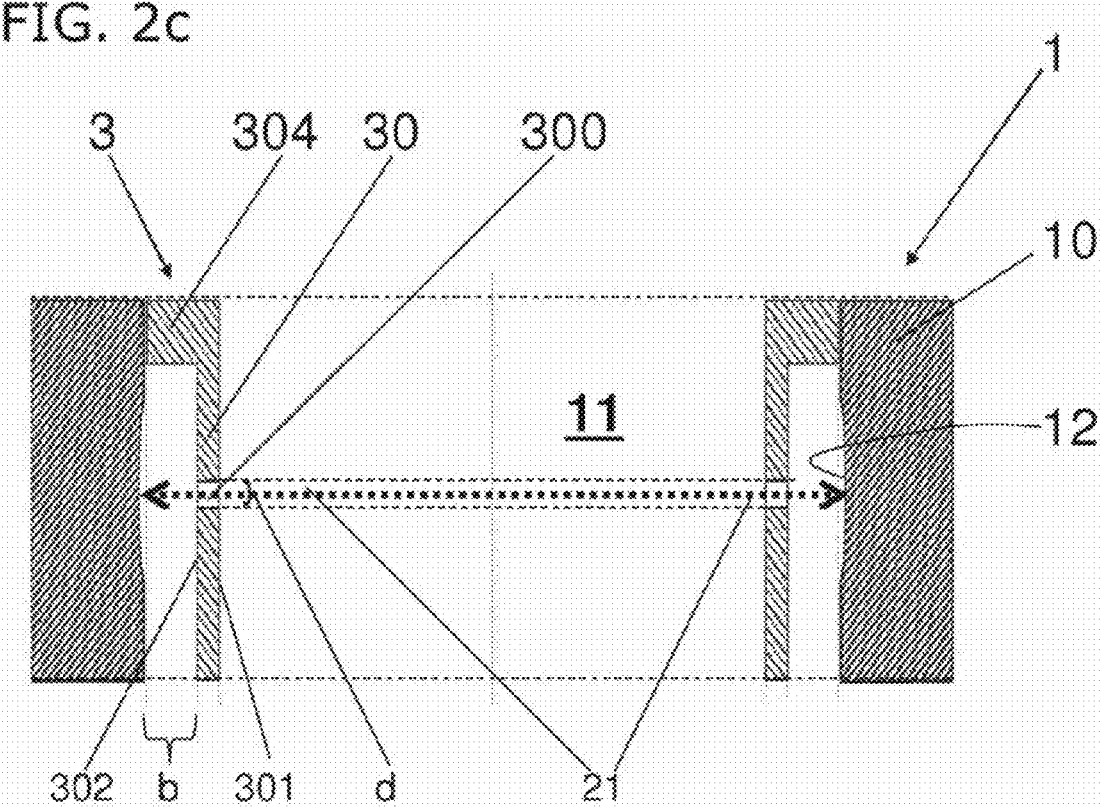

According to the sectional view of FIG. 2c the absorption mask 3 shows a mask wall 30 with an integrally moulded shroud 304. This shroud 304 is a thickening in the mask wall 30 which prevents the contact of the second side 302 with the reflective surface 12 to avoid scratches on the reflective surface 12. Because of using this shroud 304 the absorption mask 3 can be mounted into the internal space 11 with a distance b greater than zero between the second side 302 and the reflective surface 12. The mask wall 30 of the used absorption mask 3 has to be adapted to the form of the reflective surface 12 of the used multi-pass optical cell 1. Due to a chosen wall thickness t which is sufficient, the absorption mask 3 is mountable free standing and rotatably fixed in the internal space 11.

The apertures 300 are arranged in one radial plane showing identical cross-sectional areas, with identical minimum aperture diameters d. Because the calculated reflection spot pattern 211 is positioned in one radial plane, due to the ring geometry of the used multi-pass cell 1. For all embodiments of the absorption mask 3 the size of the minimum aperture diameter d should be greater than the beam diameter of the initial beam 20, in order to guarantee that only the stray light will be absorbed by the absorption mask 3.

Figure 3:
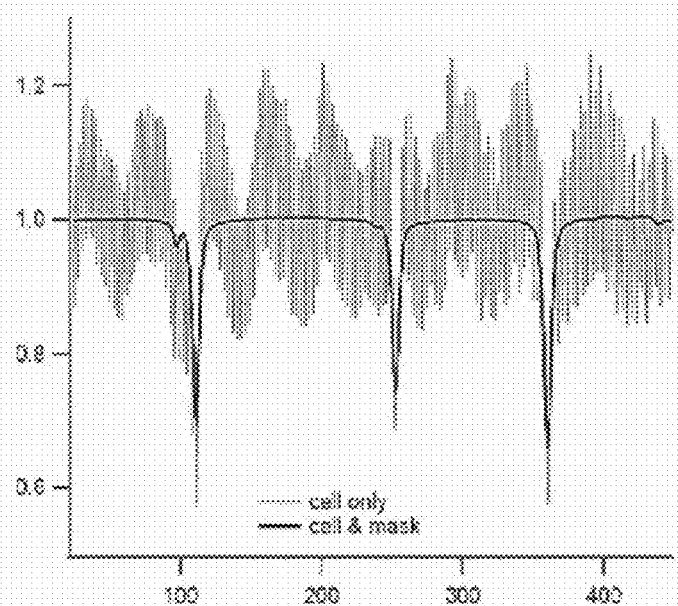
FIG. 3 shows an absorption spectrum of CO2 measured using a multi-pass cell with an absorption mask (sharp black line), and the same measurement without the use of an absorption mask (grey line).

Two absorption spectra were measured with the multi-pass optical cell 1 according to FIG. 2a, which are displayed in FIG. 3. The black continuous line in FIG. 3 was obtained with the absorption mask 3 placed inside the internal space 11 of the multi-pass optical cell 1 as depicted in FIG. 2a. The absorption features of the $CO_2$ are clearly observed in this measurement. The grey line in FIG. 3 shows the measured results taken under identical conditions, but with the absorption mask 3 removed from the multi-pass optical cell 1. The absorption features of the $CO_2$ are covered by strong fringes induced by the interference of the main optical beam with stray light.

Figure 4A:
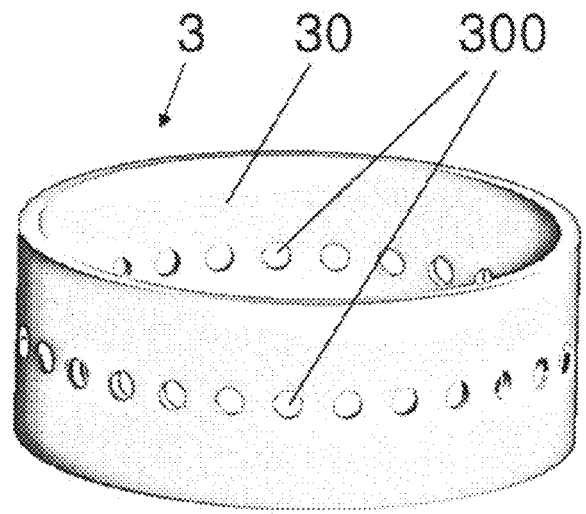

The absorption mask 3 can be varied in its design. FIG. 4a shows a closed ring form absorption mask 3 with an even mask wall 30 comprising twenty-nine apertures 300, with identical cross sections. The apertures 300 are equally distributed over the mask wall 30 in the optical plain. The apertures 300 are located in such a way, that the initial beam 20 and the reflected beams 21 can be reflected n times before the main optical beam exits the multi-pass cell 1 through the beam exit 14.

Figure 4B:
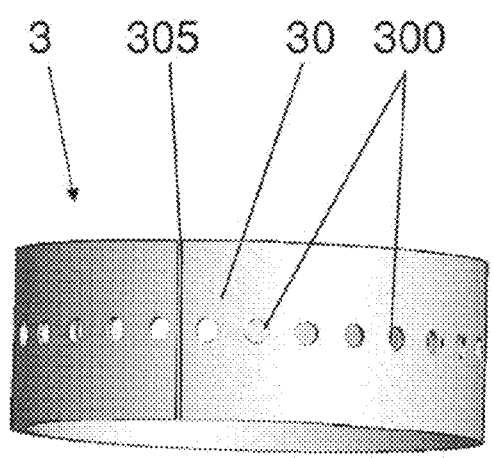

For simplified insertion of the optical mask 3 into the internal space 11 of the multi-pass cell 1, the absorption mask 3 shows an open ring form with a ring opening 305 in FIG. 4b. Due to a flexible material the absorption mask 3 is elastically shapeable. In the relaxed state, the absorption mask 3 can adapt to the reflective surface 12 and is pressed in a rotatably fixed manner to the reflective surface 12. Depending on the wall thickness t of the mask wall 30 the absorption mask 3 can be flexible. If a wall thickness t of two millimeters or less, the flexibility allows the adaption to the reflective surface 12 by a prestressing, and therewith allows a mounting of this mask 3 in a rotatably fixed manner on the reflective surface 12.

Figure 4C:
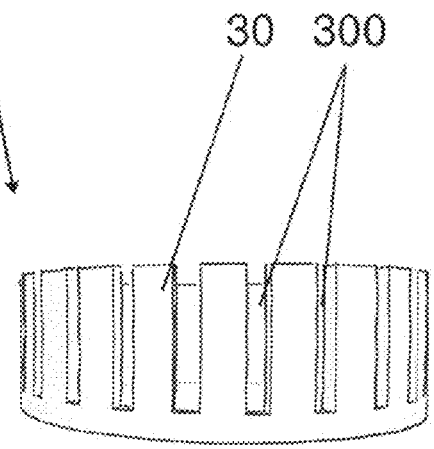
FIG. 4c shows a schematic perspective view of another embodiment of an absorption mask comprising notches in the form of slots.

In another embodiment of the absorption mask 3 the apertures 300 are elongated showing a rectangular slit as depicted in FIG. 4c. If the main optical beam is reflected in a radial plane of the reflective surface 12, the partly covering of the reflective surface 12 with such an optical mask 3 is sufficient.

Experiments showed that the shape of the apertures 300 can be circular, elliptic, rectangular or slotted. The minimum diameter has to be greater than the diameter of the initial beam 20 and the locations of the apertures 300 have to be adapted to the used multi-pass cell 1 more precisely to the geometry of the cell and the angle of incidence of the initial beam 20. The different shapes of the apertures 300 are independent of the chosen wall thickness t.

Our experiments have shown that an absorption mask 3 is especially efficient when used in a multi-pass optical cell 1 with a toroidal ring mirror 12 for laser absorption spectroscopy. These multi-pass optical cells 1 are attractive in applications where space and/or weight are limiting factors. Furthermore, the small detection volume in ring mirror absorption cells allows for rapid gas exchange. This makes these multi-pass optical cells 1 attractive for applications where a fast response is wanted.

If the absorption mask 3 is adapted, it can be used in every multi-pass optical cell 1 for laser absorption spectroscopy, so it is not limited to any specific type of cell.

Figure 5:
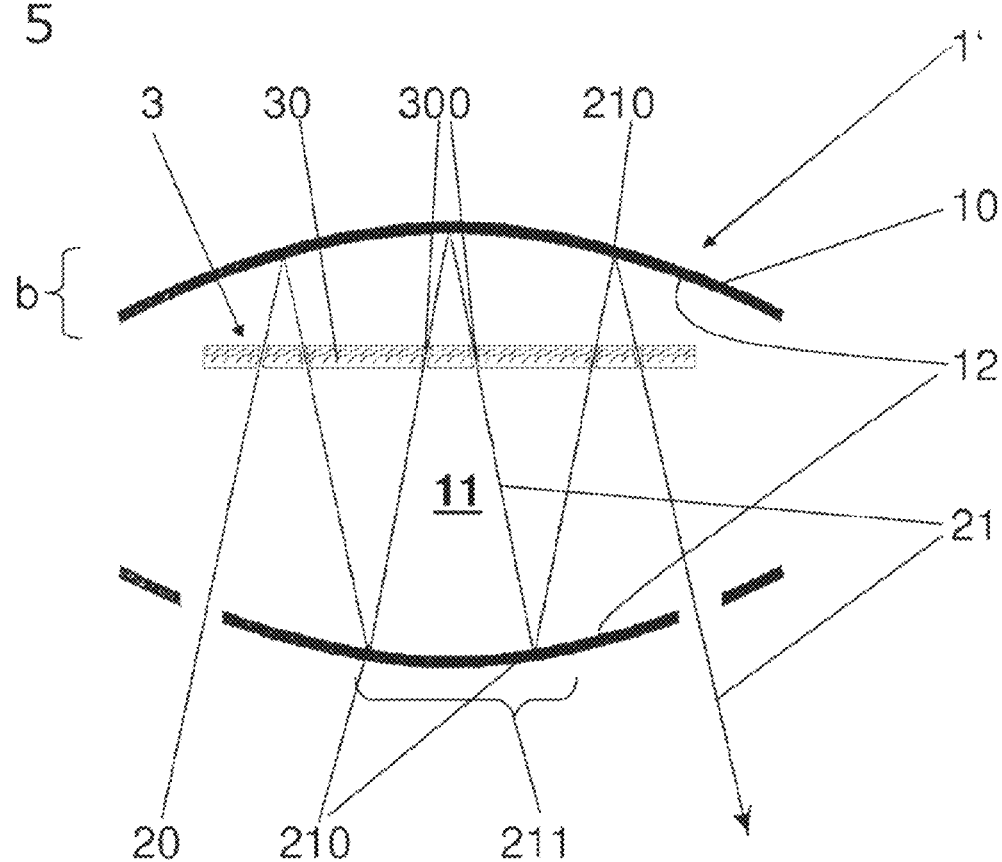
FIG. 5 shows a sectional view of another monolithic multi-pass optical cell with an absorption mask located in the internal space of the cell, separated from the reflective surface.

Another variant of the absorption mask 3 is the freestanding mask wall 30 in the internal space 11 of the multi-pass optical cell 1' according to FIG. 5. The plane mask wall 30 is standing with a distance b between the second side 302 and the reflective surface 12 greater than zero. Due to the displacement the incoming beam of each reflection spot 210 and the reflected beam are passing through different apertures 300.

Figure 6:
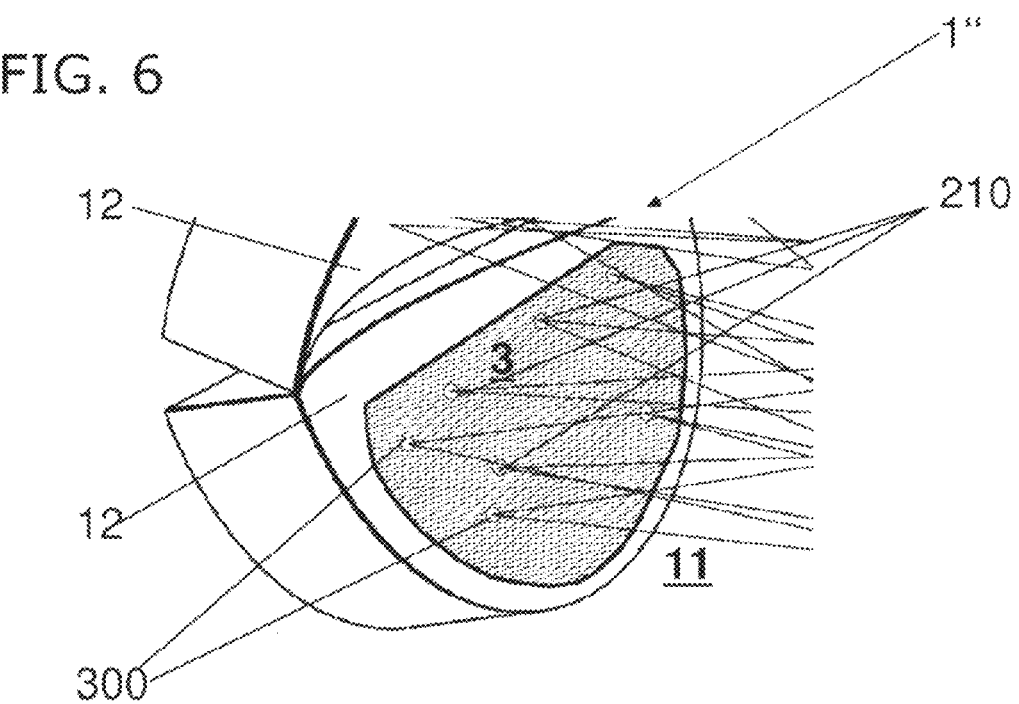
FIG. 6 shows a perspective view of another multi-pass optical cell design, with an absorption mask in form of a thin flexible layer directly glued onto one reflective surface of the multi-pass optical cell.

In FIG. 6 a multi-pass optical cell 1'' with two pairs of splitted spherical mirrors as reflective surfaces 12 is partly presented. The splitted pairs of mirrors are tilted inward along the optical axis. This setup leads to a special propagation path of the main optical beam through the internal space 11 of the multi-pass optical cell 1'. Due to the propagation path of the main optical beam a very dense reflection spot pattern 211 results. This can be determined with mathematical methods, from knowing the fixed geometry of the multi-pass optical cell 1' and the used angle of incidence. Because the reflection spot pattern 211 is known, an absorption mask 3 with a number of apertures 300 positioned according to the reflection spot pattern 211 in form of a foil can be created. The shown absorption mask 3 has to be placed rotatably fixed on at least one of the reflective surfaces 12 with distance b equal 0, in such a manner that the apertures 300 are located at the positions of the expected reflection spots 210. Because of the fact that the reflection spot's diameter in a multi-pass optical cell 1'' according to FIG. 6 vary throughout the propagation of the beam, the cross sectional areas of apertures 300 may vary.

Absorption mask 3 in form of a foil or sheet with a wall thickness t of at least 100 μm can be used. This foil 3 with well-directed apertures 300 can be self-adhesive or glued on the at least one reflective surface 12 of the multi-pass optical cell 1'. Also the mounting has to lead to a rotatably fixed absorption mask 3.

In another embodiment the absorption mask 3 could be a coating, directly deposited on the at least one reflective surface 12 with well-directed apertures 300 left open. In all embodiments an exact positioning has to be carried out, in order to place the apertures 300 at the positions of the calculated reflection spot pattern 211.

The absorption mask 3 has a shape which allows positioning it in the internal space 11 or in particular on the at least one reflective surface 12 of the multi-pass optical cell 1, 1' with high accuracy and repeatability. On the one hand, the shape of the mask 3 allows the main optical beam in the multi-pass optical cell 1 to freely pass through it. On the other hand, the mask 3 is shaped such that it effectively blocks unwanted stray light. Thereby, fringes due to interference phenomena are suppressed by inhibiting the propagation of stray light.

Another not shown embodiment is an absorption mask 3 with a wall thickness t as large that the absorption mask 3 is a solid block in the internal space 11, filling the internal space 11. The apertures 300 are arranged in the mask wall 30 in shape of channels through the solid block adapted to the anticipated reflection spot pattern 211 of the used multi-pass optical cell 1 and the calculated propagation path of the light. The fabrication is more complicated but the absorption mask 3 provides a very good absorption of infrared light. A free standing rotatably fixed absorption mask 3 can be reached with a high path to volume ratio.

Our invention is an inset for the state of the art multi-pass optical cells 1 acting as an absorption mask 3. The absorption mask 3 respectively the mask wall 30 comprises an absorber material in form of a pure plastic material, in particular a synthetic or semi-synthetic thermoplastic, in particular from the polyolefin group or a duroplast. Also compounds of these materials are possible, where the wall thickness t has to be sufficient in order to absorb infrared radiation. The wall thickness t used lay in the millimeter range.

Experiments showed that a mask wall 30 comprising Polyoxymethylene (POM) or POM copolymer (POM-C) showed sufficient absorption results. The rigidity of Polyoxymethylene is sufficient and can be machined using milling or drilling methods. Other thermoplastic materials, for example Polyetheretherketone (PEEK), Polyethylene (PE) or Polypropylene (PP) are also usable. The absorption mask 3 has to be inherently stable, if placed in a distance to the reflective surface 12. If the absorption mask 3 is exposed to gases, which are analysed, the absorption mask 3 has to be chemical inert.

The absorption mask 3 can also comprise particles or pigments of an infrared absorber material adapted to the light used in the absorption spectroscopy.

The reflective surface 12 can be blackened with paints, anodised or chemically etched coatings. For example, Nextel Velvet Black Coating 811-21—manufactured by Mankiewicz Gebr. & Co. (Hamburg, Germany) can be used, where the paints pigments comprised approximately 20% carbon black and 80% silicon dioxide are used.

In general usable dyes for infrared absorption belonging to the polymethine group, silicate minerals, metal oxides or semiconductor oxides.

LIST OF REFERENCE NUMERALS 1 multi-pass optical cell (ring mirror cell)
  10 cell body
  11 internal space
  12 reflective surface/ring mirror face
  13 beam entrance
  14 beam exit
  20 initial beam
  21 reflected beam
    210 reflection spot
    211 reflection spot pattern
    n number of reflections
3 absorption mask
  30 mask wall
    300 aperture
    301 first side
    302 second side
    303 bore hole
    304 shroud
    305 ring opening
    d aperture diameter
    m aperture number
    t wall thickness
    b distance between second side and reflective surface
QCL quantum cascade laser
RO reflective objective
OAP off-axis parabolic mirrors
L lens
M mirror
QCD quantum cascade detector

The invention claimed is:

1. A multi-pass optical cell with an internal space for laser spectroscopy, wherein the multi-pass optical cell comprises an absorption mask which is permanently or removable mountable in the internal space in a rotatably fixed manner, where in a mask wall a plurality of apertures is formed, in which the position of each aperture is adapted to a predefinable propagation path of a main optical beam and/or a resulting reflection spot pattern defined by the geometry of the multi-pass optical cell and the used angle of incidence of an initial beam, so that each aperture is traversable by the main optical beam from a first side to a second side.

2. The multi-pass optical cell according to claim 1, wherein the absorption mask exhibits a thickness of the mask wall of at least 100 µm.

3. The multi-pass optical cell according to claim 1, wherein the absorption mask comprises plastic material, in particular a synthetic or semi-synthetic thermoplastic, in particular from the polyolefin group or duroplast.

4. The multi-pass optical cell according to claim 3, wherein the absorption mask comprises Polyoxymethylene (POM) or Polyoxymethylene-copolymer (POM-C).

5. The multi-pass optical cell according to claim 1, wherein the absorption mask has a one-piece closed ring form and is formed self-supporting and dimensionally stable.

6. The multi-pass optical cell according to claim 5, wherein the absorption mask comprises handling means for mounting and unmounting of the absorption mask into the internal space of the multi-pass optical cell.

7. The multi-pass optical cell according to claim 1, wherein the absorption mask has a one-piece open ring form and is self-supporting and dimensionally stable.

8. The multi-pass optical cell according to claim 1, wherein the absorption mask is a coating comprising a plurality of uncoated areas forming the apertures on the at least one reflective surface of the multi-pass optical cell.

9. The multi-pass optical cell according to claim 1, wherein the absorption mask is formed as a foil or a sheet comprising a plurality of left open apertures.

10. The multi-pass optical cell according to claim 1, wherein the area cross-sections of the apertures are performed circular, elliptic, rectangular or slotted.

11. The multi-pass optical cell according to claim 10, wherein the absorption mask is permanently attached to at least one reflective surface of the multi-pass optical cell.

12. An absorption mask positionable in the internal space of a multi-pass optical cell for laser spectroscopy, wherein
the absorption mask comprises an absorber material adapted to the light used in the absorption spectroscopy and
the absorption mask is permanently or removable mountable in the internal space in a rotatably fixed manner, where
in a mask wall a plurality of apertures with fixed cross-sectional areas is formed in a laminary distributed way,
in which the position of each aperture is adapted to a predefinable propagation path of a main optical beam and/or a resulting reflection spot pattern defined by the geometry of the used multi-pass optical cell and the used angle of incidence of an initial beam, so that each aperture is traversable by the main optical beam from a first side to a second side.

13. A method for reducing interference fringes in laser spectroscopy measurements using a multi-pass optical cell having an internal space, wherein
an infrared radiation absorption mask with a mask wall in which a plurality of apertures with fixed cross-sectional areas is formed in a laminary distributed way,
in which the position of each aperture is adapted to a predefinable propagation path of a main optical beam and/or a resulting reflection spot pattern defined by the geometry of the used multi-pass optical cell and the used angle of incidence of an initial beam, is mounted permanently or removable in the internal space in a rotatably fixed manner, and wherein at least one reflective surface of the multi-pass optical cell is partly covered while the main optical beam can pass unhindered through the apertures.

* * * * *